United States Patent [19]
Hill et al.

[11] Patent Number: 5,372,947
[45] Date of Patent: Dec. 13, 1994

[54] ASSAY FOR AN ALDEHYDE OR A COMPOUND CAPABLE OF RELEASING AN ALDEHYDE

[75] Inventors: Martyn W. Hill, Saffron Walden; Dennis F. Sharman, West Wratting; Peter D. Recton, Huntingdon, all of United Kingdom

[73] Assignee: CTS Biocides Ltd., Cambridge, England

[21] Appl. No.: 961,329

[22] Filed: Oct. 15, 1992

[30] Foreign Application Priority Data

| Apr. 10, 1990 | [GB] | United Kingdom | 9008100.1 |
| May 8, 1990 | [GB] | United Kingdom | 9010278.1 |
| Nov. 30, 1990 | [GB] | United Kingdom | 9026054.8 |
| Oct. 30, 1991 | [GB] | United Kingdom | 9123056.5 |

[51] Int. Cl.$^5$ .......................................... G01N 33/00
[52] U.S. Cl. ................... 436/128; 436/130; 436/164; 436/175
[58] Field of Search ............... 436/128, 130, 164, 175, 436/177

[56] References Cited

U.S. PATENT DOCUMENTS

| 4,036,589 | 7/1977 | King | 436/130 X |
| 4,201,693 | 5/1980 | Hurt et al. | 436/128 |
| 4,471,055 | 9/1984 | Opp | 436/128 |
| 4,588,696 | 5/1986 | Eskelson | 436/128 X |
| 4,643,980 | 2/1987 | Witonsky et al. | 436/128 |
| 4,753,891 | 6/1988 | Thompson et al. | 436/128 X |

FOREIGN PATENT DOCUMENTS

0016578 10/1980 European Pat. Off. .

OTHER PUBLICATIONS

"Etude Comparative de la Fixation Sur Les Heterogreffes de Quelques Aldehydes Employes Pour Leur Tannage", J. Blass, C. Verriest, A. Leau, H. Detruit & M. Weiss; Pathologie-Biologie; Sep. 1974; vol. 22, No. 7; pp. 593–601.

"The Mechanism of the Reaction of the Nash and the Sawicki Aldehyde Reagent"; Bruce Compton & William Purdy; Can J. Chem.; 1980; vol. 58; pp. 2207–2211.

Sawicki et al. "The 3-Methyl-2-Benzothiazolone Hydrazone Test"-Analytical Chemistry, vol. 33, No. 1, Jan. 1961, pp. 93–96.

Primary Examiner—James C. Housel
Assistant Examiner—Maureen M. Wallenhorst
Attorney, Agent, or Firm—Oliff & Berridge

[57] ABSTRACT

An aqueous sample containing methylenebisthiocyanate or another compound capable of releasing an aldehyde is assayed by determining the amount of aldehyde released by conversion with respect to a sample from which existing aldehydes have been separated. An aqueous sample containing glutaraldehyde or another aldehyde which having at least 2 C atoms is assayed by adding an agent which gives a water-insoluble complex, and determining the amount of complex or, after regeneration, the aldehyde.

37 Claims, No Drawings

ASSAY FOR AN ALDEHYDE OR A COMPOUND CAPABLE OF RELEASING AN ALDEHYDE

RELATIONSHIP TO EARLIER APPLICATION

This is a continuation-in-part application of Serial No. PCT/GB91/00554, filed Apr. 9, 1991.

FIELD OF THE INVENTION

This invention relates to an assay for compounds which are, or can be converted to, aldehydes.

BACKGROUND OF THE INVENTION

Known aldehyde tests include the Sawicki and Purpald reactions. Both these known reactions, and especially the latter, are good for assaying formaldehyde. They are less sensitive, to varying degrees, to other aldehydes. Moreover, the Purpald reaction requires alkali, and may therefore be experimentally-undesirable.

Known biocides include cationic surfactants, such as tributyltetradecylphosphonium chloride (e.g. as sold under trade mark name Bellacide 350), glutaraldehyde and methylene-bisthiocyanate (MBTC). They are used in cooling towers, in order to control organism such as Legionella, in paper-making and in other aqueous environments. It is an object behind this invention to monitor the level of such compounds in the water. The invention is based, at least in part, on the realisation that MBTC releases formaldehyde under alkaline conditions such as those that prevail in cooling towers. The Purpald reaction is clearly unsuitable in these circumstances, since it cannot distinguish between MBTC and any free formaldehyde with which such a compound may be in equilibrium or with any formaldehyde from another source.

SUMMARY OF THE INVENTION

According to the present invention, a compound capable of forming an aldehyde upon reaction under alkaline or other given conditions (described herein as an aldehyde-releaser), and free aldehyde in an aqueous sample are distinguished. One aspect of the invention is a method which comprises:

in a first sub-sample, converting the aldehyde-releaser to aldehyde;

in a second sub-sample, separating the aldehyde-releaser and aldehyde; and determining the difference between the respective amounts of aldehyde obtained from the first and second sub-samples.

In this method, the amount of aldehyde obtained from the first sub-sample corresponds to the total amount of aldehyde-releaser and free aldehyde (which may include any aldehyde already present in the sample). The amount of aldehyde obtained from the second sub-sample corresponds to free aldehyde only, and the difference between the two amounts therefore corresponds to the amount of aldehyde-releaser.

A second aspect of the invention is a method which comprises:

separating the aldehyde-releaser and aldehyde;

converting the aldehyde-free aldehyde-releaser to aldehyde; and determining the amount of aldehyde obtained by conversion.

If the aldehyde is formaldehyde, it can be determined by the Purpald or Sawicki reaction. This is less satisfactory for an aldehyde having at least 2, 3 or more carbon atoms, e.g. glutaraldehyde. According to a further aspect of the invention, such an aldehyde is assayed by reacting an aqueous sample containing the aldehyde with an agent with which the aldehyde reacts to form a water-insoluble complex, adding a reagent that gives a colour on reaction with the complex, and determining the colour.

DETAILED DESCRIPTION OF THE INVENTION

The use of a complexing agent as described above provides one means of separating aldehyde from aldehyde-releaser. Alternatively, they may be separated by contacting the appropriate sample with an anion-exchange resin, bisulphite or other immobilised medium that retards either the aldehyde or the aldehyde-releaser; if it is then necessary or desired to assay the bound aldehyde or bound aldehyde-releaser, the bound species may be eluted.

If a complexing agent is used, it should be added in an amount sufficient to precipitate all free aldehyde, e.g. free formaldehyde (or glutaraldehyde, acetaldehyde, propionaldehyde or other aldehyde). Then it may be necessary to remove excess complexing agent in the system, e.g. to use a filtrate obtained by removing the excess complexing agent. This can be achieved by adjusting the conditions so that the excess reagent becomes insoluble. The filtrate thus obtained can be subjected to alkaline hydrolysis or any other reaction that releases the aldehyde and allows determination of the releaser.

In one embodiment, the utility of the novel method is based on the realisation that the aldehyde, but not the releaser, will form a water-insoluble complex with compounds such as substituted 1,2-diaminoethanes which themselves are readily assayed by reaction with a suitable reagent, specifically a diazo compound, to give a characteristic colour. Specific complexing agents that can be used are 1,2-dianilino-1,2-diphenylethane and 1,2-dianilinoethane (Wanzlick's reagent).

In this case, the assay can suitably be conducted by forming the complex, filtering the system, e.g. through a syringe filter, washing the complex residue, solubilising the complex, and adding a suitable diazo compound (of which many are known). Thorough washing of the residue is desirable; it is preferred to use dilute acetic acid. The solubilising agent may be 1M HCl, optionally in admixture with methanol.

The formation/physical properties of the complex may be enhanced by salting out or another procedure such as adding a polymer that reduces its adherent tendencies, thus facilitating precipitation and recovery.

The complexing agent serves to concentrate aldehyde in the sample under test. An aldehyde that would give a reaction of low sensitivity to, say, Purpald reagent in the original sample may, after concentration, be so assayed.

A preferred procedure is to separate the aldehyde-releaser and the aldehyde by bringing the sample into contact with a suitably immobilised reagent, e.g. an anion-exchange resin which binds/retards the aldehyde-releaser. The bound species can subsequently be released by elution: for example, aqueous NaCl will serve to elute MBTC from an anion-exchange resin. The releaser can then be assayed. Alternatively, the aldehyde that is not immobilised may be compared with total aldehyde that can be generated by the sample.

Formaldehyde that is released can of course be assayed by the Sawicki or Purpald reaction.

The most preferred procedure for separating aldehyde-releaser and aldehyde comprises forming a complex of the aldehyde-releaser that does not release aldehyde. The complexing material is preferably a cationic surfactant. In a particularly preferred aspect of the invention, this material is, or has the characteristics of, tributyltetradecylphosphonium chloride, i.e. Bellacide, which has been found to interact, perhaps sterically or physically, quantitatively with MBTC. Other cationic surfactants having the same property are dodecyltrimethylammonium bromide, cetylpyridinium bromide and (quaternised) alkyldimethylbenzylammonium chloride which is available under the trade name Hyamine. Other quaternary compounds, and non-ionic and zwiterionic surfactants, are less satisfactory.

The resultant complex can be in the form of micelles, so that the MBTC is resistant to hydrolysis, i.e. unavailable for conversion to aldehyde. The aldehyde-releaser is thus "immobilised" in situ.

According to a further aspect of the present invention, the total aldehyde is measured after first disassociating the aldehyde-releaser from any complex of the type described above. This is based on a realisation that formation of the complex is reversible. For example, lauryl sulfate, perhaps owing to its charges being complementary to that of an anionic surfactant, releases MBTC from a Bellacide-MBTC complex. More generally, therefore, the compound that releases the aldehyde-releaser from the complex may be any that preferentially complexes with the surfactant or other complexing material.

For any given aqueous system, it cannot necessarily be assumed that the aldehyde-releaser is non-complexed. The user will therefore usually wish to employ both of the techniques described herein.

This invention has been described primarily with a view to assaying MBTC. In view of the interaction that has been found, it will be appreciated that a derived technique may be used to assay for Bellacide or other cationic biocides.

For use in the invention, a kit may be provided comprising Bellacide or another material that complexes the aldehyde-releaser, lauryl sulfate or another substance that releases the aldehyde-releaser from such a complex, and alkali or another agent that will release aldehyde from the aldehyde-releaser.

The novel assay is simply used, because of the colorimetric reaction. The colour obtained can be read by the eye, quite satisfactorily. Alternatively, it may be matched against a standard, e.g. in a colour comparator (of the type produced by Lovibond) in which different shades are provided on a disc and correspond to calibrated concentrations of the compound being assayed. The disc is rotated until the one colour showing matches that provided by the adjacent sample.

The following Examples illustrate the respective aspects of the invention.

EXAMPLE 1 (GLUTARALDEHYDE ASSAY)

The following steps were conducted:
1. Close syringe and filter by means of a 3-way tap and pipette into syringe 6 ml water to be tested for its glutaraldehyde content (or 6 ml RO water to which appropriate quantities of glutaraldehyde have been added).
2. Add 0.4 ml Wanzlick's reagent (22 mg/ml 4M acetic acid). Mix well, wait 20 minutes.
3. Add 1 ml 3M NaCl solution, mix well, wait 30 seconds.
4. Open tap on bottom of syringe and allow liquid to pass through the Whatman 0.1 μm Puradisc filter in the filter unit; discard filtrate.
5. Wash precipitate (glutaraldehyde-Wanzlick complex) on the filter disc with 7.5 ml 0.25M acetic acid. Discard filtrate.
6. Repeat step 5. Close tap on bottom of syringe.
7. Add 3 ml 1M HCl to the syringe and shake for 1 minute to dissolve any of the complex stuck to the wall of the syringe. Open the tap. The acid is then pushed slowly through the filter. The crystalline glutaraldehyde-Wanzlick complex on the filter dissolves. Collect the filtrate in a test tube.
8. Adjust filtrate to pH 3.5 by titration with 3.75M NaOH.
9. Add 0.4 ml 4M acetic acid and mix.
10. Add 0.15 ml Superonic Polymer (0.1% in RO water). Mix.
11. Add 0.2 ml Fast Scarlet GG solution (10 mg/ml in RO water): mix and wait for 5 minutes.
12. Take out 1.5 ml into test tube.
13. Add 1.5 ml conc. HCl; mix; wait for 2 minutes.
14. Read light absorption in colorimeter at 490 nm.

Optical densities are reported in comparison with water so that the O.D. of reagent blanks can be compared with the values obtained with the substance under consideration.

Example 2 (MBTC Assay)

The following steps were conducted:
1. pipette into plastic test tube de-ionised water followed by the required volume of MBTC "working solution"; final volume: 1 ml. (If a test on a water sample is to be carried out, use 1 ml of the water to be tested for its MBTC content).
2. add 1 ml of 5M NaOH, mix well by flicking the tube with finger and thumb (or shaking) and wait 5 min.
3. add 0.5 ml Purpald reagent (10 mg/ml in 0.5M HCl), mix and allow 5 min for the formation of the first purple color complex.
4. add 0.3 ml of NaIO$_4$ solution (21.4 mg/ml water); mix, wait 1–5 min.
5. read optical density (O.D.) of the deep purple solution at 550 nm in a WPA CO 210 colorimeter; use silica or polystyrene cuvettes.

The absorption spectrum of the color complex formed by MBTC with the Purpald reagent, after oxidation with NaIO$_4$, depends upon the amount of MBTC; the maximum absorbance is always at 550 nm. For the estimation of MBTC in water, a linear response is obtained; a typical calibration curve for MBTC (stock solution, for example, 50 mg/ml DMF) obtained by the above method, can be derived from the following Table.

| MBTC (μg/sample) | O.D. - blank at 550 nm | | | |
|---|---|---|---|---|
| 1 | 0.06 | 0.05 | 0.08 | 0.08 |
| 2 | 0.14 | 0.12 | 0.16 | 0.14 |
| 3 | 0.21 | 0.19 | 0.22 | 0.22 |
| 4 | 0.29 | 0.27 | 0.25 | 0.29 |
| 5 | 0.37 | 0.35 | 0.37 | 0.36 |
| 6 | — | — | 0.44 | 0.43 |
| 8 | 0.58 | 0.56 | 0.57 | 0.57 |

| MBTC (μg/sample) | O.D. - blank at 550 nm | | | |
|---|---|---|---|---|
| 10 | 0.68 | 0.68 | 0.72 | 0.72 |

Example 3 (MBTC Assay)

The following steps were used:

Place 1.5 ml lauryl sulfate (Test)/1.5 ml Bellacide (Blank) in a 13.5 mm cell. The lauryl sulfate is provided as 40 μg/ml (sodium salt) (Sigma) in 0.04M acetic acid.

Fill each cell to the 5 ml mark with sample.

To each cell add 3.5 ml NaOH/EDTA. Mix.

To each cell add 1.75 ml Purpald (10 mg/ml, Sigma, in 0.5M hydrochloric acid). Wait 5 mins.

To each cell add 1 ml sodium periodate. Mix. Wait for 1–2 mins and match blank to M1 disc. Match test to M1 disc. Test-blank=ppm MBTC.

Comparator: Blank and test matched in comparator against cooling water only blank.

Example 4 (MBTC Assay)

The following steps were conducted:

1. Pipette into two plastic test tubes, separately, 1 ml of the water sample (or the required volume of MBTC working solution, i.e. 50 mg/ml in DMF, made up to 1 ml with deionized water)
2. To one tube, add 0.5 ml of 0.1 mg/ml lauryl sulfonate (sodium salt) in RO water and mix well (termed 'solution A').
3. To the other tube, add 0.5 ml of 4 mg/ml Bellacide in RO water and mix well (termed 'solution B').

The following steps 4–6 are followed for both solutions A and B (separately).

4. Add 1.5 ml of 0.15M ethylenediaminetetraacetic acid in 3.33M sodium hydroxide and mix thoroughly.
5. Add 0.5 ml of 10 mg/ml Purpald in 0.5M hydrochloric acid. Mix and wait for 5 minutes.
6. Add 0.3 ml of 21 mg/ml sodium periodate. Mix and read the optical density (O.D.) of the deep purple solution after 30 seconds at 550 nm in a WPA CO 210 colorimeter.
7. O.D. of solution A-O.D. of solution B=O.D. of MBTC

Example 5 (MBTC Assay)

The procedure of Example 4 was repeated but, instead of using a colorimeter, was adapted for use in a Lovibond comparator. NaOH was used at 5M and EDTA at 0.2M. MBTC is made up in one part (w/v) N-methylpyrrolidone and 3 parts (w/v) diethylene gylcol and diluted with R.O. water. The following steps were conducted:

1. To a 3.5 mm cell, add 1.5 ml Bellacide (4 mg/ml in RO water), and fill the cell up to the 5 ml mark with sample. This is the Blank.
2. To a 13.5 mm cell, add 1.5 ml lauryl sulfate (0.1 mg/ml lauryl sulfate in R.O. water, and fill the cell up to the 5 ml mark with sample. This is the Test sample.

To both samples:

3. Add 3.5 ml 5M NaOH in 0.2M EDTA. Mix thoroughly.
4. Add 1.75 ml Purpald (10 mg/ml in 0.5M hydrochloric acid). Wait 5 minutes.
5. Add 1 ml sodium periodate (21 mg/ml in R.O. water). Mix and wait for 1–2 minutes, preferably 5 min. The color is stable for this period.
6. Place blank cell in left-hand compartment and test cell in right-hand compartment and rotate disc until color match is obtained.

This procedure provides a good test for 0–10 ppm biocide (OD range 0–0.55). The same results are obtained in tap water and RO water. No problem has been encountered with real water samples.

What we claim is:

1. A method of assaying an aqueous sample for a first compound capable of forming an aldehyde upon reaction under given conditions, which sample also includes free aldehyde, which comprises the steps of:

in a first sub-sample of said aqueous sample, forming aldehyde from said first compound, and then measuring the total amount of free aldehyde in said first sub-sample wherein the total amount of free aldehyde in said first sub-sample comprises free aldehyde originally present in the first sub-sample as well as the aldehyde formed from the first compound;

in a second sub-sample of said aqueous sample, separating said first compound and free aldehyde;

measuring the amount of free aldehyde separated from said second sub-sample; and determining the difference between the respective measured amounts of free aldehyde in the first and second sub-samples so as to obtain a measure of the aldehyde formed from the first compound in the first sub-sample.

2. The method of claim 1, wherein the step of separating said first compound and free aldehyde in the second sub-sample comprises contacting said second sub-sample with an anion-exchange resin or another insolubilised medium that retards said first compound.

3. The method of claim 1, wherein the step of separating said first compound and free aldehyde in the second sub-sample comprises adding to said second sub-sample an agent with which the free aldehyde reacts to form a water-insoluble complex.

4. The method of claim 3, which comprises the additional steps of removing excess complexing agent; regenerating free aldehyde from said complex; and determining the amount of the regenerated free aldehyde.

5. The method of claim 3, which additionally comprises determining the amount of said complex.

6. The method of claim 3, wherein said complex gives a color on reaction with a suitable reagent.

7. The method of claim 6, wherein said reagent is a diazo compound.

8. The method of claim 3, wherein said complexing agent is Wanzlick's reagent or an analogue thereof.

9. The method of claim 1, wherein said first compound and free aldehyde in the second sub-sample are separated by contacting said second sub-sample with a material that complexes said first compound.

10. The method of claim 9, wherein said material is a cationic surfactant.

11. The method of claim 10, wherein said cationic surfactant is tributyltetradecylphosphonium chloride.

12. The method of claim 1, wherein the first compound in either or each sub-sample is complexed with tributyltetradecylphosphonium chloride and wherein the method additionally comprises the step of adding to either or each sub-sample a substance capable of disassociating said complex.

13. The method of claim 12, wherein said substance is lauryl sulfate.

14. The method of claim 1, wherein the free aldehyde and aldehyde formed from said first compound are formaldehyde.

15. The method of claim 14, wherein each measurement of free formaldehyde in each sub-sample comprises performing the Purpald or Sawicki reaction.

16. The method of claim 1, wherein said first compound forms aldehyde under alkaline conditions.

17. The method of claim 1, wherein said first compound is methylenebisthiocyanate.

18. A method of assaying an aqueous sample for a first compound capable of forming an aldehyde upon reaction under given conditions, which sample also comprises free aldehyde, which comprises the steps of:
separating said first compound and said free aldehyde in said aqueous sample;
forming aldehyde from the separated first compound; and
determining the amount of aldehyde formed.

19. The method of claim 18, wherein the step of separating said first compound and free aldehyde comprises contacting said aqueous sample with an anion-exchange resin or another insolubilised medium that retards said first compound.

20. The method of claim 18, wherein the step of separating said first compound and free aldehyde comprises adding to said aqueous sample an agent with which the free aldehyde reacts to form a water-insoluble complex.

21. The method of claim 20, which additionally comprises determining the amount of said complex.

22. The method of claim 20, wherein said complex gives a color on reaction with a suitable reagent.

23. The method of claim 20, wherein said complexing agent is Wanzlick's reagent or an analogue thereof.

24. The method of claim 18, wherein said first compound and free aldehyde are separated by contacting said aqueous sample with a material that complexes said first compound.

25. The method of claim 24, wherein said material is a cationic surfactant.

26. The method of claim 18, wherein the first compound in said aqueous sample is complexed with tributyltetradecyl-phosphonium chloride and wherein the method additionally comprises the step of adding to said aqueous sample a substance capable of disassociating said complex.

27. The method of claim 18, wherein the free aldehyde and aldehyde formed from said first compound are formaldehyde.

28. The method of claim 18, wherein said first compound forms aldehyde under alkaline conditions.

29. The method of claim 18, wherein said first compound is methylene-bisthiocyanate.

30. A method of assaying an aqueous sample for a free aldehyde having at least 2 carbon atoms, which sample also comprises a first compound capable of forming an aldehyde upon reaction under given conditions, which comprises the steps of:
adding to the aqueous sample an agent with which said free aldehyde reacts to form a water-insoluble complex so as to isolate the free aldehyde from said first compound;
separating the complex and adding thereto a reagent that gives a color on reaction with said complex; and
determining the color as an indication of the free aldehyde present in the aqueous sample.

31. The method of claim 29, wherein said reagent is a diazo compound.

32. The method of claim 29, wherein said complexing agent is Wanzlick's reagent or an analogue thereof.

33. The method of claim 30, wherein the aldehyde having at least 2 carbon atoms is glutaraldehyde.

34. A method of assaying an aqueous sample for a free aldehyde having at least 2 carbon atoms, which sample also comprises a first compound capable of forming an aldehyde upon reaction under given conditions, which comprises the steps of:
adding to the aqueous sample an agent with which the free aldehyde reacts to form a water-insoluble complex so as to isolate the free aldehyde from said first compound;
separating the complex and releasing free aldehyde from the complex; and
determining the amount of the released free aldehyde.

35. The method of claim 34, wherein said complexing agent is Wanzlick's reagent or an analogue thereof.

36. The method of claim 34, wherein the aldehyde having at least 2 carbon atoms is glutaraldehyde.

37. An assay kit, suitable for use in a method for assaying a first compound capable of forming an aldehyde upon reaction under given conditions in an aqueous sample, which comprises a first container containing a material that complexes said first compound but not free aldehyde, a second container containing a substance capable of disassociating a complex of said first compound and said material, and a third container containing a compound capable of forming an aldehyde from said first compound upon reaction.

* * * * *